US006486363B1

(12) United States Patent
Berg et al.

(10) Patent No.: US 6,486,363 B1
(45) Date of Patent: *Nov. 26, 2002

(54) PROCESS FOR THE MANUFACTURE OF BIS (4-HYDROXYARYL)ALKANES

(75) Inventors: Klaus Berg, Krefeld (DE); Hans-Josef Buysch, Krefeld (DE); Alfred Eitel, Dormagen (DE); Gerhard Fennhoff, Willich (DE); Georg Malamet, Krefeld (DE); Clauss Wulff, Krefeld (DE)

(73) Assignee: Bayer Aktiengesellschaft (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1108 days.

(21) Appl. No.: 08/679,730

(22) Filed: Jul. 12, 1996

(30) Foreign Application Priority Data

Jul. 18, 1995 (DE) .......................................... 195 26 088

(51) Int. Cl.[7] .............................................. C07C 39/16
(52) U.S. Cl. ....................................... 568/728; 568/727
(58) Field of Search ................................... 568/727, 728

(56) References Cited

U.S. PATENT DOCUMENTS

| 2,775,620 | A | * | 12/1956 | Williamson et al. | ........ 260/619 |
| 4,301,305 | A | * | 11/1981 | Kiedik et al. | ................ 568/727 |
| 4,391,997 | A | | 7/1983 | Mendiratta | |
| 4,400,555 | A | * | 8/1983 | Mendiratta et al. | .......... 568/728 |
| 5,399,789 | A | * | 3/1995 | Cipullo | ........................ 568/702 |

FOREIGN PATENT DOCUMENTS

| EP | 0 342 758 | 11/1989 |
| EP | 0 616 993 | 9/1994 |
| GB | 785079 | 10/1957 |

* cited by examiner

Primary Examiner—Barbara P. Badio
(74) Attorney, Agent, or Firm—Connolly Bove Lodge & Hutz LLP

(57) ABSTRACT

The present invention relates to a process for the manufacture of bis(4-hydroxyaryl)alkanes by heterogeneous acid-catalyzed reaction of aromatic hydroxy compounds with ketones in reactors connected in series, which in the direction of advancing conversion are operated with rising temperature and optionally with increasing loading.

3 Claims, 1 Drawing Sheet

PROCESS FOR THE MANUFACTURE OF BIS (4-HYDROXYARYL)ALKANES

Figure 1:
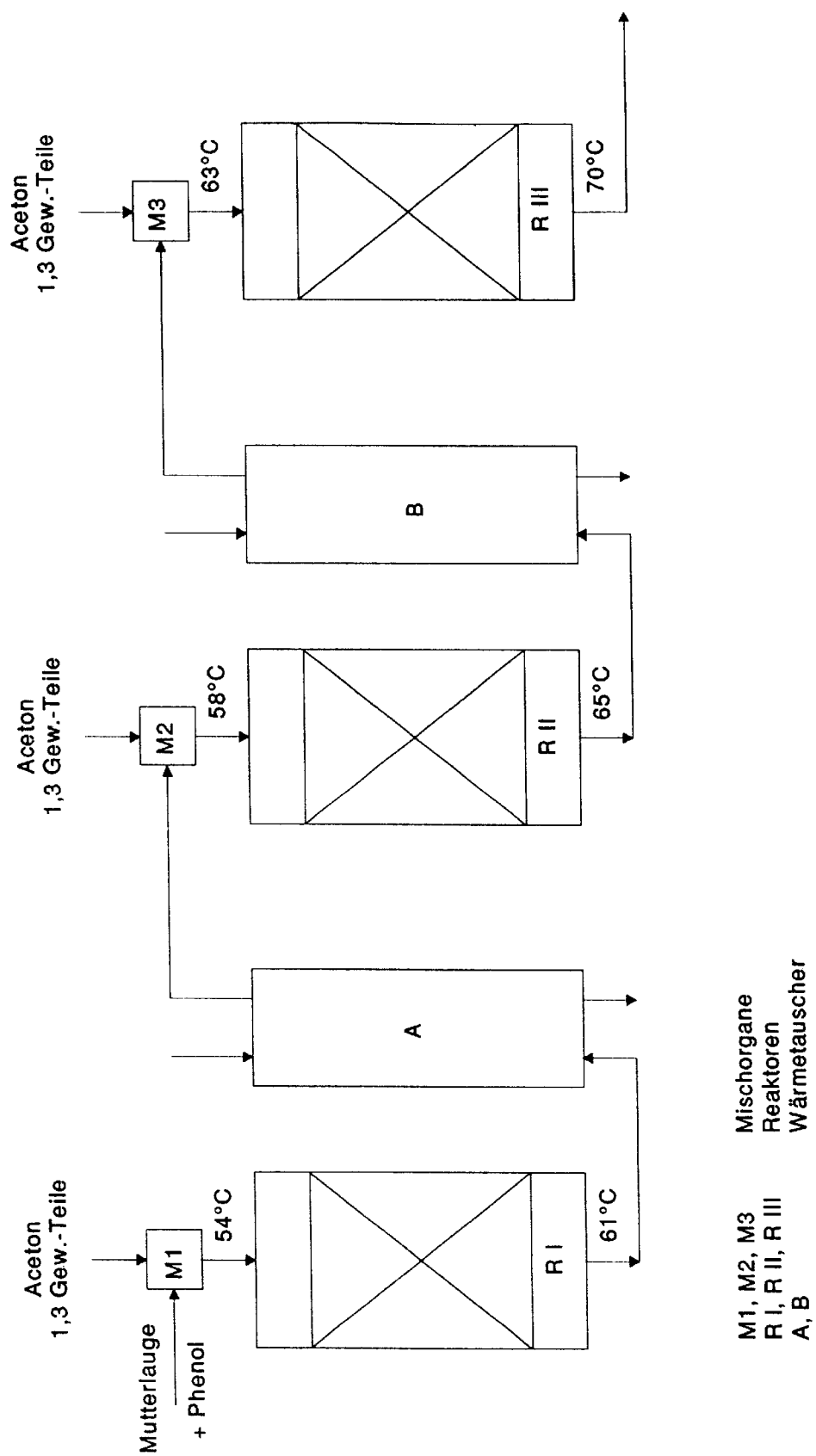

The present invention relates to a process for the manufacture of bis(4-hydroxyaryl)alkanes by heterogeneous acid-catalyzed reaction of aromatic hydroxy compounds with ketones in reactors connected in series, which are operated with rising temperature and optionally with increasing loading in the direction of advancing conversion.

It is known in a process for the manufacture of bis(4-hydroxyaryl)alkanes from phenols and ketones to distribute the required amount of ketone to several reactors connected in series. U.S. Pat. No. 2,775,620 describes a process catalyzed with mineral acid in the homogeneous liquid phase; a heterogeneously catalyzed process with an acid ion exchanger in a fixed bed reactor follows from U.S. Pat. No. 4,400,555 (EP-A 342 758). Both documents show that by dividing up the amount of ketone the proportion of by-products is reduced, this proportion being less in the case of HCl catalysis than in the case of catalysis by ion exchangers. This is only demonstrated however, for an educt mixture of phenol and acetone. In a continuously operated production plant, however, the mother liquor obtained after separation of the bis(4-(hydroxyaryl)alkane from the reaction mixture is as a rule returned to the process. In the course of this, isomers and by-products can concentrate, which leads to disturbances in the process, e.g. worse crystallization of the bis(4-hydroxyaryl)alkane and lower product quality.

It is therefore desirable to develop processes in which under the conditions of a continuously operated plant the lowest possible proportions of isomers and by-products are formed.

A process has now been discovered for the manufacture of bis(4-(hydroxyaryl)alkanes by heterogeneous acid-catalyzed reaction of aromatic hydroxy compounds with ketones in at least two fixed bed reactors connected in series which are operated with temperature rising in the direction of advancing conversion,. wherein the total amount of ketone is divided up over the individual reactors and is distributed homogeneously in the reaction mixture before the particular catalyst beds are entered.

Suitable aromatic hydroxy compounds for the process according to the invention are not substituted in the p position and contain no second-order substituents such as cyano, carboxy or nitro groups; there may be mentioned for example phenol, o- and m-cresol, 2,6-dimethylphenol, o-tert-butylphenol, 2-methyl-6-tert-butylphenol, o-cyclohexylphenol,o-phenylphenol,o-isopropylphenol,2-methyl-6-cyclopentylphenol, o- and m-chlorophenol and 2,3,6-trimethylphenol. Phenol, o- and m-cresol, 2,6-dimethylphenol, o-tert-butylphenol and o-phenylphenol are preferred; most preferred is phenol.

Suitable ketones contain at least one aliphatic group on the carbonyl function; there may be mentioned for example acetone, methyl ethyl ketone, methyl propyl ketone, methyl isopropyl ketone, diethyl ketone, acetophenone, cyclohexanone, cyclopentanone, methyl-, dimethyl- and trimethylcyclohexanone, which also can have geminal methyl groups, like 3,3-dimethyl-5-methylcyclohexanone (hydroisophorone). Acetone, acetophenone, cyclohexanone and its homologues bearing methyl groups are preferred; most preferred is acetone.

Preferred educts for the process according to the invention are particularly also the mother liquors remaining after separation of the bis(4-hydroxyaryl)alkanes, which, after addition of the hydroxy compounds consumed and optionally removal of a certain proportion to avoid the enrichment of unwanted by-products, are returned to the process; in the case of the synthesis of bisphenol A such mother liquors contain about 78–88 wt. % phenol and 12–22 wt. % bisphenol A and by-products, which have the following composition:

| | |
|---|---|
| Bisphenol A | 40–65 wt. % |
| o,p-Bisphenol | 14–19 wt. % |
| Trisphenol | 2–6 wt. % |
| Chromans | 4–17 wt. % |
| 1,3,3-Trimethyldihydroxyphenylindans | 3–13 wt. % |
| other by-products | 3–15 wt. % |

The molar ratio of aromatic hydroxy compound to ketone is in general 5:1 to 25:1, preferably 7:1 to 20:1, most preferably 8:1 to 18:1, relative to the overall reaction.

The educt mixture used can contain small amounts of water, preferably less than 1, most preferably less than 0.6 and especially less than 0.3 wt. %.

The ion exchanger resins used as catalysts and the mercapto compounds used as cocatalysts are well known to the person skilled in the art (U.S. Pat. Nos. 2,468,982; 2,623,908; 2,775,620; DE-OS 3 619 450; 3 727 641).

In continuous operation, before each reaction cycle the amount of aromatic hydroxy compound consumed in the preceding cycle is readded to the reaction mixture. The amount of ketone required for the adjustment to the required molar ratio of hydroxy compound and ketone is divided up over the n reactors of the production plant, approximately the nth part of the total amount of ketone being added to the reaction mixture before each reactor. The deviation from this value for the individual reactors can be absolutely ±15%, preferably ±10% and most preferably ±5 %.

The number of reactors is at least 2 and for economic reasons is as a rule not more than 8, preferably not more than 6, most preferably not more than 4.

The loading, defined as the amount (in kg) of educt mixture per liter catalyst in the operating condition (swollen) and per hour, is about 0.1 to 2.0 per reactor, preferably 0.15 to 1.7, most preferably 0.19 to 1.5 kg/l·h. The loading should as a rule be so chosen that the conversion of acetone after the last reactor is at least 75%, better ≧83%, preferably ≧90% and most preferably ≧95%.

It is not necessary to operate all reactors with the same loading. Rather, it is advantageous for a further increase in selectivity to raise the loading of the reactors from reactor to reactor in the direction of increasing conversion. For example in a plant with three reactors, the first reactor can be operated with 0.3, the second reactor with 0.6 and the third reactor with 0.8 kg/l·h.

For an effective reduction of the amount of by-product it is very important that before a particular catalyst bed is entered the ketone is distributed completely homogeneously in the reaction mixture, which can be achieved by the use of nozzles, static mixers, stirred tanks, centrifugal pumps or other mixing apparatuses familiar to the person skilled in the art.

The reactors connected in series are operated with temperatures rising in the direction of advancing conversion. Between start and end of the reactor cascade a rising temperature profile is set in the temperature range of 40 to 100° C., preferably 45 to 90° C., most preferably 50 to 85° C. The temperature differences from one reactor to the next are as a general rule the smaller the more reactors have to be passed through. It is also possible to operate two successive reactors with the same temperature.

Since no intermixing occurs in fixed bed reactors and dissipation of the heat of reaction from the reaction mixture is difficult, such reactors are as a rule operated adiabatically, which leads to the heating of the reaction mixture. It is therefore usually expedient to cool the reaction mixture between the individual reactors, care having to be taken that the crystallizing-out of bis(4-hydroxyaryl)alkane, which would lead to a blockage of the tubing, is avoided.

The invention will be illustrated by example in the following pages.

EXAMPLE 1

The experimental set-up is shown diagrammatically in FIG. 1. The numerical values in the Figure are to be considered as examples. A mixture of 98.7 parts by weight of a mother liquor from current bisphenol A production, to which the phenol consumed had been readded, and 1.3 parts by weight of acetone, which had been well mixed in a container, was charged to the first of a series of three fixed bed reactors connected in series and filled with a sulphonated polystyrene resin, cross-linked with 2% divinylbenzene and loaded with 5% cysteamine, with an average temperature of 61° C. and a loading of 0.2 kg/l·h, under nitrogen through the catalyst bed.

The reaction mixture leaving the reactor was collected, again well mixed with 1.3 parts by weight of acetone, and passed, with an average temperature of 66° C. and a loading of 0.2 kg/l·h, under nitrogen through the second reactor bed.

To the product mixture discharging from this reactor, 1.3 parts by weight of acetone were again admixed and the mixture, with an average temperature of 71° C. and a loading of 0.2 kg/l·h, passed through the third reactor.

The acetone conversion was complete. The experiment was carried out for 535 h. The average composition of the reaction product after the third reactor obtained by daily analyses is shown in Table 1.

EXAMPLE 2

In an experiment analogous to Example 1, the total amount of 3.9 parts by weight of acetone was admixed to the reaction mixture before reactor I. The reaction mixture was fed at a loading of 0.2 kg/l·h and converted at an average temperature of 70° C.

The acetone conversion was complete. The experiment was carried out for 468 h. The average composition of the reaction product after the reactor obtained by daily analyses is shown in Table 1.

EXAMPLE 3

On carrying out the experiment analogously to Example 2 at an average temperature of 65° C. the reaction mixture crystallized out in the reactor. The experiment had to be abandoned.

TABLE 1

|  | o,p-BP | BPA | Trisphenol | Chromans | Remaining by-products |
|---|---|---|---|---|---|
| Educt in 85 parts phenol | 17.74 | 56.31 | 4.37 | 6.31 | 15.27 |

TABLE 1-continued

|  | o,p-BP | BPA | Trisphenol | Chromans | Remaining by-products |
|---|---|---|---|---|---|
| Example 1 | 8.10 | 80.40 | 1.83 | 2.76 | 6.91 |
| Example 2 | 9.80 | 78.40 | 2.22 | 3.16 | 6.42 |
| Example 3 | Abandoned because of crystallization in the reactor | | | | |

The experiments show that the selectivity for bisphenol A (BPA) in the continuous operation is raised by 2% as a result of the divided feeding of acetone, homogeneous distribution of the acetone in the reaction mixture to be converted and rising temperature along the reaction train in the direction of advancing conversion.

EXAMPLE 4

Example 1 was repeated with a mother liquor from the current BPA production that had a different composition from that in Example 1. The compositions of the educt and of the product mixture are shown in Table 2.

EXAMPLE 5

Example 2 was repeated with the mother liquor used in Example 4. The composition of the reaction mixture is shown in Table 2.

EXAMPLE 6

An experiment analogous to Example 4 was carried out, in which all reactors were operated at an average temperature of 70° C. The composition of the reaction mixture is shown in Table 2.

TABLE 2

|  | o,p-BP | BPA | Trisphenol | Chromans | Remaining by-products |
|---|---|---|---|---|---|
| Educt in 85 parts phenol | 16.75 | 58.19 | 3.75 | 7.80 | 13.46 |
| Example 4 | 7.95 | 79.25 | 1.82 | 3.80 | 7.18 |
| Example 5 | 9.19 | 77.26 | 2.14 | 4.00 | 7.41 |
| Example 6 | 7.23 | 78.20 | 1.80 | 4.56 | 8.21 |

The experimental durations in Examples 4 to 6 were from 250 to 270 h. It is clear that, despite a different composition, the increase in selectivity is again about 2%. In the comparison of Example 4 and Example 6, the effect of the temperature gradient on the selectivity is clear.

EXAMPLE 7

Example 1 was repeated with a mother liquor from current BPA production which had a composition other than in Example 1. The acetone conversion was complete; the experimental duration was 108 h. The composition of the educt and product mixtures are shown in Table 3.

EXAMPLE 8

Example 4 was repeated with a loading of 0.4 kg/l·h. The acetone conversion was complete; the experimental duration was 80 h. The composition of the product mixtures is shown in Table 3.

EXAMPLE 9

Example 7 was repeated with a loading of 0.6 kg/l·h. The acetone conversion exceeded 98%; the experimental duration was 98 h. The composition of the product mixture is shown in Table 3.

EXAMPLE 10

An experiment was carried out analogously to Example 7, Reactor I being operated with a loading of 0.2 kg/l·h, Reactor II with a loading of 0.4 kg/l·h and Reactor III with a loading of 0.6 kg/l·h. The acetone conversion was >98% and the experimental duration was 82 h. The composition of the product mixture is shown in Table 3.

TABLE 3

|  | o,p-BP | BPA | Trisphenol | Chromans | Remaining by-products |
|---|---|---|---|---|---|
| Educt in 85 parts phenol | 16.69 | 59.29 | 3.60 | 8.09 | 12.33 |
| Example 7 | 7.97 | 79.77 | 1.81 | 3.95 | 6.50 |
| Example 8 | 8.20 | 79.79 | 1.85 | 3.90 | 6.26 |
| Example 9 | 8.48 | 79.46 | 1.95 | 3.87 | 6.24 |
| Example 10 | 8.18 | 79.93 | 1.83 | 3.85 | 6.21 |

It is evident that the selectivity is maintained, even at high loading, and by arrangement of a loading gradient in the direction of advancing conversion can rise further.

EXAMPLE 11

Experiment 1 was repeated; pure phenol instead of a mother liquor from the production of BPA was used in the educt mixture. Table 4 shows the composition of the product mixture after the third reactor.

EXAMPLE 12

Experiment 2 was repeated; pure phenol instead of a mother liquor from the production of BPA was used in the educt mixture. Table 4 shows the composition of the product mixture after the third reactor.

TABLE 4

|  | o,p-BP | BPA | Trisphenol | Chromans | Remaining by-products |
|---|---|---|---|---|---|
| Example 11 | 5.68 | 93.50 | 0.47 | 0.12 | 0.23 |
| Example 12 | 6.76 | 91.90 | 0.48 | 0.46 | 0.40 |

Also when pure phenol is used instead of a mother liquor from the production of BPA, the proportion of bisphenol A in the product mixture can rise by homogeneous distribution of the acetone additions in the reaction mixture and the arrangement of a temperature gradient in the direction of advancing conversion.

What is claimed is:

1. Process for the manufacture of bis(4-hydroxyaryl) alkanes by heterogeneous acid-catalyzed reaction of aromatic hydroxy compounds with ketones in at least two reactors connected in series, which are operated with temperatures rising in the direction of advancing conversion, wherein the total amount of ketone is divided up over the individual reactors and is homogeneously distributed in the reaction mixture before the particular catalyst beds are entered, and wherein the reactors are operated with loading increasing in the direction of advancing conversion.

2. A process as in claim 1 wherein the number of reactors is four.

3. A process as in claim 1 wherein the process is continuous and before each reaction cycle an amount of aromatic hydroxy compound consumed in a preceding cycle is added to the reaction mixture.

* * * * *